(12) United States Patent
Dengler et al.

(10) Patent No.: US 9,365,452 B2
(45) Date of Patent: Jun. 14, 2016

(54) CLAY-COMPATIBLE ADDITIVE FOR CONSTRUCTION CHEMICALS

(71) Applicant: Construction Research & Technology GmbH, Trostberg (DE)

(72) Inventors: Joachim Dengler, Tacherting (DE); Barbara Mittermaier, Tacherting (DE)

(73) Assignee: Construction Research & Technology GmbH, Trostberg (DE)

(*) Notice: Subject to any disclaimer, the term of this patent is extended or adjusted under 35 U.S.C. 154(b) by 0 days.

(21) Appl. No.: 14/408,792

(22) PCT Filed: Jun. 7, 2013

(86) PCT No.: PCT/EP2013/061816
§ 371 (c)(1),
(2) Date: Dec. 17, 2014

(87) PCT Pub. No.: WO2014/001064
PCT Pub. Date: Jan. 3, 2014

(65) Prior Publication Data
US 2015/0183688 A1    Jul. 2, 2015

(30) Foreign Application Priority Data
Jun. 26, 2012 (EP) .................................. 12173505

(51) Int. Cl.
| | | |
|---|---|---|
| *C04B 16/00* | (2006.01) | |
| *C04B 28/02* | (2006.01) | |
| *C08G 8/20* | (2006.01) | |
| *C08G 8/28* | (2006.01) | |
| *C08L 61/00* | (2006.01) | |
| *C08L 61/04* | (2006.01) | |
| *C08L 61/14* | (2006.01) | |
| *C08L 61/34* | (2006.01) | |
| *C04B 24/22* | (2006.01) | |
| *C04B 24/24* | (2006.01) | |
| *C04B 28/14* | (2006.01) | |
| *C04B 28/16* | (2006.01) | |
| *C04B 40/00* | (2006.01) | |
| *C07F 9/02* | (2006.01) | |

(Continued)

(52) U.S. Cl.
CPC ............... *C04B 16/00* (2013.01); *C04B 24/22* (2013.01); *C04B 24/243* (2013.01); *C04B 28/02* (2013.01); *C04B 28/14* (2013.01); *C04B 28/16* (2013.01); *C04B 40/0039* (2013.01); *C07F 9/02* (2013.01); *C07F 9/091* (2013.01); *C08G 8/20* (2013.01); *C08G 8/28* (2013.01); *C08G 63/06* (2013.01); *C08K 3/28* (2013.01); *C08K 3/34* (2013.01); *C08K 5/06* (2013.01); *C08K 5/09* (2013.01); *C08K 5/17* (2013.01); *C08K 5/42* (2013.01); *C08K 5/52* (2013.01); *C08K 5/521* (2013.01); *C08L 61/00* (2013.01); *C08L 61/04* (2013.01); *C08L 61/14* (2013.01); *C08L 61/34* (2013.01); *C08L 67/04* (2013.01); *C08K 2003/287* (2013.01); *Y02W 30/92* (2015.05); *Y02W 30/94* (2015.05)

(58) Field of Classification Search
CPC ...... C04B 24/22; C04B 24/023; C04B 24/06; C04B 24/10; C04B 24/122; C04B 24/18; C04B 24/223; C04B 24/226; C04B 24/2647; C04B 24/38; C04B 24/243; C04B 22/149; C04B 22/085; C04B 22/16; C04B 22/0086; C04B 28/02; C04B 28/14; C04B 28/16; C04B 40/0039; C04B 14/10; C04B 14/108; C04B 18/08; C04B 18/141; C04B 2103/0088; C04B 2103/50; C04B 16/00; C07F 9/02; C07F 9/091; C08G 63/06; C08G 8/20; C08G 8/28; C08K 2003/287; C08K 3/28; C08K 3/34; C08K 5/06; C08K 5/09; C08K 5/17; C08K 5/42; C08K 5/52; C08K 5/521; C08L 61/00; C08L 61/04; C08L 61/14; C08L 61/34; C08L 67/04; Y02W 30/92; Y02W 30/94
See application file for complete search history.

(56) References Cited

U.S. PATENT DOCUMENTS

| | | | |
|---|---|---|---|
| 1,989,951 | A | 2/1935 | Süssenguth |
| 2,640,043 | A | 5/1953 | Sturm |

(Continued)

FOREIGN PATENT DOCUMENTS

| | | |
|---|---|---|
| DE | 2 341 923 | 3/1975 |
| DE | 31 44 673 A1 | 5/1983 |

(Continued)

OTHER PUBLICATIONS

PCT/EP2013/061816—International Search Report, mailed Aug. 16, 2013.

(Continued)

*Primary Examiner* — Satya Sastri
(74) *Attorney, Agent, or Firm* — Curatolo Sidoti Co., LPA; Joseph G. Curatolo; Salvatore A. Sidoti

(57) ABSTRACT

The invention relates to a monomer-based condensation product, wherein the monomers comprising at least one monomer having an aldehyde moiety and at least one monomer having a ketone moiety, which is carrying at least one non-aromatic moiety and the condensation product comprises at least one moiety from the series of phosphono, sulphino, sulpho, sulphamido, sulphoxy, sulphoalkyloxy, sulphinoalkyloxy and phosphonooxy groups and/or salts thereof, wherein the monomers further comprising gallic acid. Additionally disclosed are the preparation and the use of these condensation products in chemical products for the construction industry.

15 Claims, No Drawings

(51) Int. Cl.

| | |
|---|---|
| *C07F 9/09* | (2006.01) |
| *C08G 63/06* | (2006.01) |
| *C08K 3/28* | (2006.01) |
| *C08K 3/34* | (2006.01) |
| *C08K 5/06* | (2006.01) |
| *C08K 5/09* | (2006.01) |
| *C08K 5/17* | (2006.01) |
| *C08K 5/42* | (2006.01) |
| *C08K 5/52* | (2006.01) |
| *C08K 5/521* | (2006.01) |
| *C08L 67/04* | (2006.01) |

(56) References Cited

U.S. PATENT DOCUMENTS

| | | | |
|---|---|---|---|
| 3,016,092 A | | 1/1962 | Harvey et al. |
| 3,972,723 A | * | 8/1976 | Balle ................. C04B 24/22 106/677 |
| 4,585,853 A | | 4/1986 | Plank et al. |
| 4,657,593 A | * | 4/1987 | Aignesberger ...... B01F 17/0028 106/487 |
| 4,666,979 A | * | 5/1987 | Plank ........................ C08G 6/02 525/515 |
| 5,421,881 A | * | 6/1995 | Rodrigues ............... C04B 24/16 106/806 |
| 5,705,599 A | * | 1/1998 | Felixberger ........... B01F 17/005 524/542 |

FOREIGN PATENT DOCUMENTS

| | | |
|---|---|---|
| DE | 38 25 530 A1 | 2/1989 |
| EP | 0 078 938 A1 | 5/1983 |
| EP | 0 126 320 A2 | 11/1984 |
| GB | 2 156 801 A | 10/1985 |

OTHER PUBLICATIONS

PCT/EP2013/061816—International Written Opinion, mailed Aug. 16, 2013.

PCT/EP2013/061816—International Preliminary Report on Patentability, issued Dec. 31, 2014.

* cited by examiner

CLAY-COMPATIBLE ADDITIVE FOR CONSTRUCTION CHEMICALS

CROSS REFERENCE TO RELATED APPLICATIONS

This application is a national stage application of International Application No. PCT/EP2013/061816, filed 7 Jun. 2013, which claims priority from European Patent Application No. 12173505.4, filed 26 Jun. 2012, from which applications priority is claimed, and which are incorporated herein by reference.

The invention relates to a monomer-based condensation product, the monomers comprising aldehydes, ketones having at least one non-aromatic moiety and gallic acid and the condensation product comprises at least one moiety from the series of phosphono, sulphino, sulpho, sulphamido, sulphoxy, sulphoalkyloxy, sulphinoalkyloxy and phosphonooxy groups and/or salts thereof. Additionally disclosed are the preparation and the use of these condensation products in chemical products for the construction industry.

DE-B 2 341 923 discloses readily water-soluble condensation products of cycloalkanones and formaldehyde, using sodium sulphite as the compound which introduces acid groups. A disadvantage of these condensation products, however, is their low thermal stability. Thus, for example, when a solution of the cycloalkanone-formaldehyde condensation products is concentrated, even under gentle conditions (around 50° C.), largely water-insoluble compounds in powder form are produced. Other sulphonic acid-modified formaldehyde condensation products as well, based on urea, for example, undergo decomposition at temperatures around the boiling point of water. At high temperatures of the kind occurring, for example, in deep wells in the oil industry, these condensation products cannot be used.

The condensation of symmetrical or non-symmetrical ketones having acyclic aliphatic, araliphatic and/or aromatic moietys with aldehydes in the presence of sodium sulphite is known from DE 3144673. In its final stage, it leads to water-soluble resins which contain sulphite groups. The use of sodium sulphite both as alkaline catalyst and as compound which introduces acid groups allows the formation of water-soluble condensation products which are suitable, for example, as additives to inorganic binders for enhancing their properties, these products being stable even at high temperatures.

A disadvantage of such condensation products, however, is that they have a deep-red colour and, as an additive to chemical products for the construction industry, for example mortar or concrete, result in strong reddening of the surface of the cured products. Moreover, the efficiency of these condensation products as dispersants for construction chemicals mixtures comprising inorganic binders is not satisfactory.

In substantial use presently as dispersants for inorganic binder systems are polycarboxylate ethers, since they allow very good plasticizing properties and effective retention of fluidity over time (slump retention). Polycarboxylate ethers, however, have the disadvantage of being highly sensitive with regard to clays, especially smectite, and of being fully deactivated even at low levels of clay. In these inorganic binder systems, clay may be introduced, for example, via the aggregates or via limestone, and this is a major problem in many countries, owing to the natural clay content of the raw materials used. It is also known that β-naphthalenesulphonate-formaldehyde condensates (BNS) possess an acceptable clay compatibility, but have the disadvantage of a relatively low slump retention and a poor effectiveness at low water/cement ratios (<0.35).

It is an object of the present invention, therefore, to provide products which, as additives in chemical products for the construction industry, do not cause discoloration. Furthermore, the products ought to be heat-stable and ought to be suitable, for example, as additives for enhancing the properties of aqueous inorganic systems even at high temperatures. More particularly, the already good properties of the products known from the prior art, as dispersants for inorganic binders, for example, ought to be improved further. A further object of the present invention was to provide an additive for chemical products for the construction industry, comprising an inorganic binder, which has a high compatibility with respect to clays, especially smectite.

This object has been achieved by means of a monomer-based condensation product, wherein the monomers comprising I) at least one monomer having an aldehyde moiety and
II) at least one monomer having a ketone moiety, which is carrying at least one non-aromatic moiety,
and the condensation product comprises at least one moiety from the series of phosphono, sulphino, sulpho, sulphamido, sulphoxy, sulphoalkyloxy, sulphinoalkyloxy and phosphonooxy groups and/or salts thereof,
wherein the monomers further comprise
III) gallic acid.

As additives in chemical products for the construction industry, comprising an inorganic binder, the condensation products of the invention surprisingly do not lead to any discoloration to the surface of the cured products. It was also surprising that the already good properties of the condensation products known from the prior art, for example as dispersants for systems comprising inorganic binders, could be improved further. In particular, the condensation products of the invention possess a high tolerance with respect to clays. The condensation products also have a high heat-stability. They are stable in general at temperatures of up to at least 300° C. This heat-stability is retained even in the presence of water.

With more particular preference the condensation product comprises further at least one aromatic monomer from the series aminobenzenesulphonic acid, sulphanilic acid, aniline, ammoniobenzoic acid, dialkoxybenzenesulphonic acid, dialkoxybenzoic acid, pyridine, pyridinemonosulphonic acid, pyridinedisulphonic acid, pyridinecarboxylic acid and pyridinedicarboxylic acid. Particularly preferred in this context is aminobenzenesulphonic acid.

Concerning the at least one moiety from the series phosphono, sulphino, sulpho, sulphamido, sulphoxy, sulphoalkyloxy, sulphinoalkyloxy and phosphonooxy groups and/or salts thereof, it is also being possible for these groups to be bonded via nitrogen or oxygen, or via —N-alkylene or —O-alkylene bridges, and in that case, for example, they are sulphamido, sulphooxy, sulphoalkyloxy, sulphinoalkyloxy or else phosphonooxy groups. An alkyl group in these moietys possesses preferably 1 to 5 carbon atoms and is more particularly methyl or ethyl. Phosphono, sulphino and more particularly sulpho groups are preferred.

In one preferred embodiment the condensation product comprises at least one iron-salt. The iron-salt is preferably a iron(II)sulphate and/or iron(III)sulphate.

The molar ratio of gallic acid/iron-salt is preferably 2/1 to 1/10, although deviations are also possible in accordance with the specific end use.

The moiety R in R—CHO, i.e. the monomer I), may be hydrogen, an aromatic or non-aromatic cyclic or non-aromatically acyclic moiety or a carboxylic or heterocyclic moiety or else an araliphatic moiety, in which the number of carbon atoms or of carbon atoms and heteroatoms is preferably 1 to 10. Aromatic moietys are, for example, α- or β-naphthyl, phenyl or furfuryl; araliphatic moietys are, for example, benzyl or phenethyl; non-aromatic moietys are, for example, cycloalkyl and more particularly alkyl moietys, preferably having 1 to 6 carbon atoms, such as methyl, ethyl, propyl and butyl, for example. The aliphatic moietys may also be branched or unsaturated and in that case are, for example, vinyl.

The monomer I) may also be substituted by one or more substituents which do not adversely affect the condensation reaction, such as, for example, by amino, hydroxyl, alkoxy or alkoxycarbonyl groups and/or else by the acid groups that are present in the condensation products. It is also possible to use aldehydes having more than one aldehyde group, e.g. dialdehydes or trialdehydes, which in view of their heightened reactivity may in certain cases be particularly useful. In the case, for example, of the lower saturated aldehydes such as formaldehyde or acetaldehyde, it is also possible to use the polymeric forms (e.g. paraformaldehyde or paraldehyde).

In one preferred embodiment the monomer I) comprises at least one aldehyde from the series paraformaldehyde, formaldehyde, acetaldehyde, butyraldehyde, glyoxal, glutaraldehyde, benzaldehyde, naphthylaldehyde or naphthylsulphonaldehyde, 3-methoxypropionaldehyde, acetaldol, acrolein, crotonaldehyde, furfurol, 4-methoxyfurfurol, propargylaldehyde, glyoxylic acid, carboxypropanal, carboxybutanal, carboxypentanal, glucose, sucrose, cinnamaldehyde, lignins and lignosulphonates. A particularly preferred aldehyde used is formaldehyde.

Monomers II) used in accordance with the invention for the condensation product are symmetrical or non-symmetrical ketones having acyclic, aliphatic, araliphatic and/or aromatic hydrocarbon moietys, but in which at least one moiety is a non-aromatic moiety. The hydrocarbon moietys preferably possess 1 to 10 carbon atoms.

Acyclic aliphatic moietys are straight-chain or branched, unsaturated and preferably saturated alkyl moietys, such as methyl, ethyl propyl, butyl, isobutyl and nonyl, for example. Araliphatic moietys are, for example, benzyl or phenethyl, and aromatic moietys are, for example, α- or β-naphthyl, and especially phenyl.

The monomers II) may also be substituted by one or more substituents which do not adversely affect the condensation reaction, such as, for example, by amino, hydroxyl, alkoxy or alkoxycarbonyl groups and/or else by the acid groups that are present in the condensation products.

With more particular preference the monomer II) comprises at least one ketone from the series methyl ethyl ketone, acetone, diacetone alcohol, ethyl acetoacetate, laevulinic acid, methyl vinyl ketone, mesityl oxide, 2,6-dimethyl-2,5-heptadien-4-one, acetophenone, 4-methoxyacetophenone, 4-acetylbenzenesulphonic acid, diacetyl, acetylacetone, benzoylacetone and cyclohexanone. Especially preferred is acetone.

The monomers I) and monomers II) can be used in pure form, or else in the form of compounds with the compound which introduces the at least one moiety from the series of phosphono, sulphino, sulpho, sulphamido, sulphoxy, sulphoalkyloxy, sulphinoalkyloxy and phosphonooxy groups and/or salts thereof—for example, in the form of aldehyde-sulphite adduct or as a salt of hydroxymethanesulphinic acid. It is also possible to use two or more different aldehydes and/or ketones.

The total number of carbon atoms or, where appropriate, of carbon atoms and heteroatoms in the monomers I) and monomers II) used in accordance with the invention is preferably selected such as to retain the hydrophilic nature of the condensation products. It is therefore dependent on, among other factors, the number of acid groups in the condensation product, but also on the ketone/aldehyde ratio. The preferred total number for the aldehydes is 1 to 11, for the ketones 3 to 12.

The condensation product of the invention comprises the monomers preferably in the following composition:
25 to 74 mol % of monomer I),
25 to 74 mol % of monomer II) and
0.01 to 30 mol %, preferably 1 to 25 mol % and with more particular preference 5 to 20 mol % of monomer III).

The molar ratio of aldehyde/ketone/the at least one moiety from the series of phosphono, sulphino, sulpho, sulphamido, sulphoxy, sulphoalkyloxy, sulphinoalkyloxy and phosphonooxy groups and/or salts thereof/gallic acid is preferably 1/1 to 3.5/0.02 to 2/0.001 to 1, although deviations are also possible in accordance with the specific end use.

In one preferred embodiment the condensation product has a molecular weight of between 1000 and 30 000 g/mol, the molecular weight being measured by gel permeation chromatography and calibrated to a polyethylene glycol standard.

On the basis of their properties, the condensation products of the invention can be used as dispersants and, with particular preference, as plasticizers for aqueous systems.

The desired properties can be controlled here through a suitable choice of the starting compounds and of the molar proportions. Examples of aqueous systems in which products of the invention can be used advantageously include the following: inorganic binder suspensions and binder solutions, pigment dispersions and dye dispersions, dispersants for oil-in-water emulsions, aqueous kaolin suspensions or clay suspensions, and oil/water/charcoal suspensions. As a consequence of their high heat-stability, the condensation products of the invention are especially suitable as additives for inorganic binders. As dispersants they are suitable, for example, for producing flowable concrete or self-levelling screeds, and their good heat-stability also makes them suitable, in particular, for the plasticizing of deep-well cement mixtures, where a high temperature stability is required on account of the high temperatures occurring. Surface-active agents of the invention lower the surface tension of aqueous solutions and are suitable, for example, as a foamer additive for the production of foamed concrete. They can also be used as agents for introducing air pores for mortar or concrete. Another possible application lies in the mobilization of residual oil by surfactant flooding or micellar flooding in the case of tertiary oil production. As retention agents they are suitable for producing slurries of hydraulic binders that have good water retention capacity, in the case for example of deep well cement slurries or in the case of tile adhesives, and as thickeners they are very suitable, for example, in the oil industry for increasing the viscosity of aqueous solutions or suspensions.

In one preferred embodiment the condensation product of the invention is used as an additive for a building material composition which comprises an inorganic binder. It is preferred here to use 0.002% to 2% by weight, more particularly 0.01% to 1% by weight and very preferably 0.05% to 0.5% by weight of the condensation product, based on the overall inorganic solids fraction of the building material composition.

In one preferred embodiment the binder in question comprises at least one from the series portland cement, lime, gypsum, calcium sulphate hemihydrate, more particularly bassanite, anhydrous calcium sulphate, more particularly anhydrite, fly ash, blast furnace slag, pozzolans and burnt oil shale.

The term "pozzolans" in the sense of the present invention comprehends binders which do not set by themselves but instead, after storage in humid conditions, yield reaction products which develop a strength as a result of the formation of calcium hydroxide, examples of such products including fly ash, blast furnace slag, microsilica, and also natural pozzolans, such as trass, pumice, aluminas, tuff and/or ignimbrite. Other pozzolans which do not set by themselves may be ashes from the combustion of natural products, such as rice husks and grain hulls.

In one particularly preferred embodiment the condensation product of the invention may be used as a dispersant for cementitious systems or gypsum. The systems in question here may be, in particular, masonry mortars, render mortars, mortars for thermal insulation composite systems, renovating renders, jointing mortars, tile adhesives, thin-bed mortars, screed mortars, casting mortars, injection mortars, filling compounds, grouts or lining mortars (e.g. for mains water pipes). Additionally preferred is the use of the condensation products of the invention in gypsum-based filling compounds, gypsum-based self-levelling screeds or gypsum plasterboard.

The condensation product of the invention can be used here with particular advantage when the building material mixture comprises smectite, which may be introduced into the building material mixture via aggregates or limestone, for example.

In particular in comparison to polycarboxylate ether but also to 3-naphthalene-sulphonate-formaldehyde condensates, the condensation product of the invention exhibits virtually no reduction in its dispersing effect in the presence of smectite.

In one preferred embodiment the condensation product is used in building material compositions comprising between 0.1% to 20% by weight of smectite, preferably 0.5% to 15% by weight. The term "smectite" comprehends all swellable clay minerals of the dioctahedral montmorillonite series and also of the trioctahedral saponite series.

The condensation products are used preferably in the form of solutions or dispersions, more particularly in the form of aqueous solutions or dispersions. The solids content of these preparations is generally 10% to 70%, more particularly 20% to 50% by weight.

It is also possible to use two or more of the condensation products of the invention with the same, similar and/or else different activity, or mixtures thereof with one or more known additives having the same, similar and/or different activity, such as, for example, mixtures with known dispersants, surfactants or concrete admixtures. In this way it is often possible additionally to modify or differentiate the properties of the end products.

The present invention accordingly further provides a composition comprising, based on the dry mass,
10% to 99% by weight of the condensation product of the invention and also
1% to 90% by weight of at least one compound from the series polycarboxylate ethers, lignosulphonate, melamine-formaldehydesulphonate, naphthalene-formaldehydesulphonate, polyaryl ethers, phosphorylated polyalkoxylates, β-naphthalenesulphonate-formaldehyde condensates, melamine condensates, sulphanilic acid-phenolic resins, calcium nitrate, crystalline calcium silicate hydrate, phosphates, gluconates, sucrose, starch hydrolysates, triethanolamine, triisopropanolamine, diethanolisopropanolamine, ethanoldiisopropanolamine, poly(hydroxyalkylated)polyethyleneamine, N, N-bis (2-hydroxypropyl)-N-(hydroxyethyl)amine, 1-(N,N-bis(2-hydroxyethyl)amino)propan-2-ol, N,N,N',N'-tetra(2-hydroxyethyl)ethylenediamine, methyldiethanolamine, monoethanolamine, diethanolamine, monoisopropanolamine, diisopropanolamine and defoaming agents.

The condensation products of the invention can be obtained by reacting the monomers under alkaline conditions, and a one-pot reaction procedure may be followed. As embodiments of the preparation of the condensation products it is preferred to introduce monomer I) and monomer III) and a compound which introduces the at least one moiety from the series of phosphono, sulphino, sulpho, sulphamido, sulphoxy, sulphoalkyloxy, sulphinoalkyloxy and phosphonooxy groups and/or salts thereof, and then to add the monomer II).

The reaction generally sets with just gentle heating and is then exothermic, and so, in general, cooling is practiced. In order to achieve a uniform product or in particular when using starting products that are relatively unreactive, it is useful to continue heating, possibly for up to several hours.

In one preferred embodiment the monomers are reacted at a pH of 8 to 14, more particularly of 9 to 13. The pH adjustment may take place, for example, by addition of hydroxides of monovalent or divalent cations, or by introduction of a compound which introduces the at least one moiety from the series of phosphono, sulphino, sulpho, sulphamido, sulphoxy, sulphoalkyloxy, sulphinoalkyloxy and phosphonooxy groups and/or salts thereof, such as sodium sulphite, for example, which is hydrolysed with an alkaline reaction in aqueous solution.

The reaction can be carried out in both homogeneous phase and heterogeneous phase. The reaction is preferably carried out in water or in a mixture of water and a polar organic solvent, the fraction of the water being preferably at least 50% by weight. As non-aqueous solvent additions, polar organic solvents are contemplated in particular, such as alcohols or acid esters, for example. The reaction may be carried out either in an open vessel or in an autoclave, in which case it may be useful to operate in an inert gas atmosphere, e.g. under nitrogen.

The condensation products can be isolated if desired from their solutions or dispersions as obtained after the reaction; such isolation may be accomplished, for example, by concentration on a rotary evaporator or by spray drying. The solutions or dispersions obtained may alternatively be used directly as they are.

Monomers I) and monomers II) used are the aforementioned aldehydes and ketones, and mixtures of ketones and/or aldehydes can be used as well. The aldehydes and ketones may be employed either in pure form or as a compound with the compound that introduces the at least one moiety from the series of phosphono, sulphino, sulpho, sulphamido, sulphoxy, sulphoalkyloxy, sulphinoalkyloxy and phosphonooxy groups and/or salts thereof, in the form of a bisulphite addition compound, for example. They may be introduced initially both in aqueous solution and in non-aqueous solution, alcoholic solution for example, or added in these forms.

In the case of aldehydes or ketones with a short alkyl chain, the reaction is particularly rapid and exothermic, whereas a long thermal aftertreatment is required for complete reaction in the case of compounds having sterically bulky substituents, such as methyl isobutyl ketone or benzylacetone, for example.

As compounds which introduce the at least one moiety from the series phosphono, sulphino, sulpho, sulphamido, sulphoxy, sulphoalkyloxy, sulphinoalkyloxy and phosphonooxy group and/or salts thereof, it is possible to use all compounds which introduce these moietys under the condensation conditions, such as, for example, the pure salts, salts of the acids with monovalent to trivalent organic or inorganic cations or addition compounds, more particularly addition compounds with the aldehydes and ketones used in accordance with the invention. Examples thereof are sulphites, hydrogensulphites, pyrosulphites, bisulphite addition compounds of aldehydes or ketones, salts of amidosulphonic acid, taurine salts, salts of sulphanilic acid, salts of hydroxymethanesulphinic acid, salts of aminoacetic acid and salts of phosphorous acid.

The present invention produces, in particular, products which do not give rise to any discoloration when used as additives in a reasonable dosage range (<2% b.w.c) in chemical products for the construction industry that comprise an inorganic binder. This is especially advantageous, since such discoloration severely restricts the use of the existing condensation products. Moreover, these products are heat-stable and are therefore suitable even at high temperatures, for example, as additives for improving the properties of aqueous inorganic systems. Furthermore, surprisingly, it is also possible to improve further the dispersing properties by comparison with the known condensation products. Another great advantage of the condensation products of the invention is their high compatibility with respect to clays, more particularly smectite, as a result of which they can also be used in building material compositions in which the polycarboxylate ethers that are usually used do not exhibit any effect.

The examples below illustrate the advantages of the present invention.

Sodium sulphite is dissolved in the reaction solution, and ketone is added dropwise, and the mixture is stirred thoroughly. During this procedure, the temperature rises to 30-32° C. The solution is heated to 56° C.

Formaldehyde is added slowly dropwise, in the course of which the temperature ought not to exceed 70° C. Following complete addition, the temperature is raised to 90° C. and the mixture is heated for a number of hours until the desired molecular weight has been reached.

| Polymer | Ketone | Sodium sulphite | Formaldehyde (30%) | Gallic acid | Further component | Mw [g/mol] |
| --- | --- | --- | --- | --- | --- | --- |
| 1 | Acetone 1 mol | 0.43 mol | 2.5 mol | 0.15 mol | — | 15000 |
| 2 | Acetone 1 mol | 0.55 mol | 2.46 mol | 0.023 mol | Laevulinic acid 0.045 mol | 16000 |
| 3 | Acetone 1 mol | 0.51 mol | 2.91 mol | 0.023 mol | Sulphanilic acid 0.068 mol | 16400 |
| 4 | Acetone 1 mol | 0.51 mol | 2.91 mol | 0.023 mol | Salicylic acid 0.068 mol | 16400 |
| Comparative example 2 | Cyclohexanone 1 mol | 0.3 mol sodium pyrosulphite | 2.55 mol | — | — | 21000 |
| Comparative example 1 | Acetone 1 mol | 0.51 mol | 3 mol | — | — | 19000 |

EXAMPLES

Polymer Synthesis

General Procedure 40 g of water are introduced initially. Then the corresponding amount of comonomer is added. The pH is adjusted to 10.

Robustness with respect to clay impurities

The clay compatibility is demonstrated by means of a paste test.

The cement used is a CEM I 42.5R from Bernburg, from the company Schwenk Zement KG. The clay-containing mineral used is siltstone, a natural pozzolan. It contains 30% by weight of clays, especially smectites.

The cement is weighed out into a 900 ml metal beaker. The corresponding amount of water is introduced into an extra glass beaker. The water is added to the cement and the mixture is stirred for 60 seconds. The mixture is then left to stand for 60 seconds. Using a syringe, the plasticizer is added in the form of a 30% strength aqueous solution, and the paste is stirred for 180 seconds. The resultant cement paste is introduced into a mini-cone with a lower internal diameter of 40 mm, this cone standing on the wetted glass plate (Hägermann plate with diameter of 300 mm). After the cone has been lifted off, the slump is measured at three different locations, and the average is ascertained. The slump is determined after 5, 10, 20 and 30 minutes. Prior to each measurement, the mixture is briefly agitated with a spatula.

In order then to determine the clay sensitivities, the calibration reference used is commercial BNS (Melcret 500L). First of all, the level of addition of the corresponding plasticizers that is required in order to obtain a slump of d=120 mm is ascertained for a water/cement ratio (w/b) of 0.33 in a CEM I cement. These levels of addition are then used in a blend of cement and pozzolan. In the case of a mixture of 70% by weight CEM I and 30% by weight pozzolan, a water/cement ratio of 0.55 is used. From the examples shown below it is evident that plasticizers based on polycarboxylate ethers have only low compatibility with clays, but the polymers of the invention exhibit a better performance than BNS.

The mini-mortar tests show the efficiency of the polymers of the invention in comparison to conventional plasticizers.

| No. | Cement | Additive | w/b | % by weight | Slump flow [mm] 3 min | 10 min | 20 min | 30 min |
|---|---|---|---|---|---|---|---|---|
| 1 | CEM I 42.5R | Glenium Sky 623 | 0.33 | 0.07 | 127 | 100 | 87 | |
| 2 | CEM I 42.5R | BNS | 0.33 | 0.4 | 48 | | | |
| 3 | CEM I 42.5R | 1 | 0.33 | 0.4 | 78 | 59 | | |
| 4 | CEM I 42.5R | Comparative example 2 | 0.55 | 0.4 | 49 | | | |
| 5 | CEM I 42.5R | Comparative example 1 | 0.55 | 0.4 | 58 | | | |
| 6 | CEM I 42.5R/pozzolan (7/3) | Glenium Sky 623 | 0.55 | 0.07 | 58 | 41 | 40 | |
| 7 | CEM I 42.5R/pozzolan (7/3) | BNS | 0.55 | 0.4 | 82 | 75 | 72 | 68 |
| 8 | CEM I 42.5R/pozzolan (7/3) | 1 | 0.55 | 0.4 | 141 | 134 | 121 | 113 |
| 9 | CEM I 42.5R/pozzolan (7/3) | Comparative example 2 | 0.55 | 0.4 | 85 | 89 | 79 | |
| 10 | CEM I 42.5R/pozzolan (7/3) | Comparative example 1 | 0.55 | 0.4 | 136 | 124 | 104 | | min = minutes
w/b = water/cement ratio

The colour of the cured samples is investigated using mortar prisms. In this case a mortar with a water/cement ratio of 0.3 is prepared. The cement used is a class CEM I cement from the company Schwenk KG, from the Bernburg plant. The levels of addition of plasticizer that are used in this case, relative to its solids content, are 1% by weight, based on the cement content.

| Additive | Colour |
|---|---|
| 1 | Slightly yellowish discolorations |
| 2 | Slightly yellowish discolorations |
| 3 | Slightly yellowish discolorations |
| 4 | Slightly yellowish discolorations |
| Comparative example 1 | Orange-red-spotted surface |

Mini-Mortar Tests

The mini-mortar tests were carried out as follows:

Water/cement levels were set at 0.48. The sand/cement ratio selected was 2.2. The cement used was CEM I 42.5R from Bernburg, from the company Schwenk Zement KG.
Procedure:

Cement and sand are introduced in a metal beaker and stirred together. The plasticizer is dissolved in water and added to the cement mixture. The suspension is mixed at setting 1 for 30 seconds. It is then mixed at setting 2 for 60 seconds more. After a waiting time of 20 seconds, mixing takes place at setting 1 for a further 90 seconds. The mixture is introduced into a mini-cone having a lower diameter of 40 mm. After the cone has been lifted up, the slump flow is measured.

| Cement | Additive | w/b | % by weight | Slump flow [mm] 4 min | 10 min | 20 min |
|---|---|---|---|---|---|---|
| CEM I 42.5R | 1 | 0.48 | 0.35 | 24.9 | 22.2 | 19.9 |
| CEM I 42.5R | 2 | 0.48 | 0.35 | 23.2 | 21.1 | 20.0 |
| CEM I 42.5R | 3 | 0.48 | 0.35 | 23.9 | 22.6 | 22.0 |
| CEM I 42.5R | 4 | 0.48 | 0.35 | 24.1 | 22.1 | 20.0 |
| CEM I 42.5R | Comparative example 1 | 0.48 | 0.4 | 24.7 | 22.3 | 21.4 |
| CEM I 42.5R | Comparative example 2 | 0.48 | 0.8 | 24.9 | 23.0 | 22.1 | min = minutes
w/b = water/cement ratio

The mini-mortar test shows that the additives of the invention yield comparable results for slump flow, at a lower level of addition.

The invention claimed is:

1. A monomer-based condensation product, wherein the monomers comprise
   I) at least one monomer having an aldehyde moiety and
   II) at least one monomer having a ketone moiety, which carries at least one non-aromatic moiety,
   and the condensation product comprises at least one moiety selected from phosphono, sulphino, sulpho, sulphamido, sulphoxy, sulphoalkyloxy, sulphinoalkyloxy, phosphonooxy groups and salts thereof,
   characterized in that the monomers further comprise
   III) gallic acid.

2. The condensation product according to claim 1, characterized in that the condensation product further comprises at least one aromatic monomer selected from aminobenzenesulphonic acid, aniline, ammoniobenzoic acid, dialkoxybenzenesulphonic acid, dialkoxybenzoic acid, pyridine, pyridinemonosulphonic acid, pyridinedisulphonic acid, pyridinecarboxylic acid and pyridinedicarboxylic acid.

3. The condensation product according to claim 1, characterized in that the condensation product comprises at least one iron-salt.

4. The condensation product according to claim 3, characterized in that the iron-salt is iron(II)sulphate and/or iron(III)sulphate.

5. The condensation product according to claim 1, characterized in that the monomers comprise
   25 to 74 mol % of monomer I),
   25 to 74 mol % of monomer II) and
   0.01 to 30 mol % of monomer III).

6. The condensation product according to claim 1, characterized in that the monomer I) comprises at least one aldehyde selected from paraformaldehyde, formaldehyde, acetaldehyde, butyraldehyde, glyoxal, glutaraldehyde, benzaldehyde, naphthylaldehyde, naphthylsulphonaldehyde, 3-methoxypropionaldehyde, acetaldol, acrolein, crotonaldehyde, furfural, 4-methoxyfurfural, propargylaldehyde, glyoxylic acid, carboxypropanal, carboxybutanal, carboxypentanal, glucose, sucrose, cinnamaldehyde, lignins and lignosulphonates.

7. The condensation product according to claim 1, characterized in that the monomer II) comprises at least one ketone selected from methyl ethyl ketone, acetone, diacetone alcohol, ethyl acetoacetate, laevulinic acid, methyl vinyl ketone, mesityl oxide, 2,6-dimethyl-2,5-heptadien-4-one, acetophenone, 4-methoxyacetophenone, 4-acetylbenzenesulphonic acid, diacetyl, acetylacetone, benzoylacetone and cyclohexanone.

8. The condensation product according to claim 1, characterized in that the condensation product has a molecular weight of between 1000 and 30 000 g/mol and the molecular weight is measured by gel permeation chromatography and calibrated to a polyethylene glycol standard.

9. Process for preparing a condensation product according claim 1, characterized in that the monomers are reacted at a pH of 8 to 14.

10. The process for preparing a condensation product according to claim 9, characterized in that the reaction is carried out in water or in a mixture of water and a polar organic solvent.

11. A method of utilizing the condensation product according to claim 1 comprising adding the condensation product to a building material composition which comprises an inorganic binder.

12. The method according to claim 11, characterized in that 0.002% to 2% by weight of the condensation product is added, based on the overall inorganic solids fraction of the building material composition.

13. The method according to claim 11, characterized in that the building material composition comprises between 0.1% and 20% by weight of smectite.

14. The method according to claim 11, characterized in that the binder is at least one selected from portland cement, lime, gypsum, calcium sulphate hemihydrate, anhydrous calcium sulphate, flyash, blast furnace slag, pozzolans and burnt oil shale.

15. A composition comprising, based on dry mass,
10% to 99% by weight of the condensation product according to claim 1 and also
1% to 90% by weight of at least one compound selected from
polycarboxylate ethers, lignosulphonate, melamine-formaldehydesulphonate, naphthalene-formaldehydesulphonate, polyaryl ethers, phosphorylated polyalkoxylates, β-naphthalenesulphonate-formaldehyde condensates, melamine condensates, sulphanilic acid-phenolic resins, calcium nitrate, crystalline calcium silicate hydrate, phosphates, gluconates, sucrose, starch hydrolysates, triethanolamine, triisopropanolamine, diethanolisopropanolamine, ethanoldiisopropanolamine, poly(hydroxyalkylated)polyethyleneamine, N,N-bis(2-hydroxypropyl)-N-(hydroxyethyl)amine, 1-(N,N-bis(2-hydroxyethyl)-amino)propan-2-ol, N,N,N',N'-tetra(2-hydroxyethyl)ethylenediamine, methyldiethanolamine, monoethanolamine, diethanolamine, monoisopropanolamine, diisopropanolamine and defoaming agents.

* * * * *